(12) United States Patent
Geisslinger et al.

(10) Patent No.: US 8,092,829 B2
(45) Date of Patent: Jan. 10, 2012

(54) USE OF R-ARYLPROPIONIC ACIDS FOR TREATING ILLNESSES WITH A RHEUMATIC NATURE

(75) Inventors: Gerd Geisslinger, Bad Soden (DE); Sabine Grösch, Heidenrod-Egenroth (DE)

(73) Assignee: Paz Arzneimittelentwicklungsgesellschaft mbH, Frankfurt am Main (DE)

( * ) Notice: Subject to any disclaimer, the term of this patent is extended or adjusted under 35 U.S.C. 154(b) by 1171 days.

(21) Appl. No.: 10/381,320

(22) PCT Filed: Sep. 24, 2001

(86) PCT No.: PCT/EP01/11004
§ 371 (c)(1), (2), (4) Date: May 22, 2003

(87) PCT Pub. No.: WO02/24190
PCT Pub. Date: Mar. 28, 2002

(65) Prior Publication Data
US 2004/0037876 A1    Feb. 26, 2004

(30) Foreign Application Priority Data
Sep. 25, 2000    (DE) .................. 100 47 319

(51) Int. Cl.
*A61K 9/48* (2006.01)
(52) U.S. Cl. ........................ 424/452; 424/465
(58) Field of Classification Search ............ None
See application file for complete search history.

(56) References Cited

U.S. PATENT DOCUMENTS

| | | | | |
|---|---|---|---|---|
| 5,200,198 A * | 4/1993 | Geisslinger et al. | ......... | 424/489 |
| 5,206,029 A | 4/1993 | Brune et al. | | |
| 5,556,638 A | 9/1996 | Wunderlich et al. | | |
| 6,506,785 B2 * | 1/2003 | Evans et al. | .............. | 514/411 |

FOREIGN PATENT DOCUMENTS

| | | |
|---|---|---|
| CA | 2 362 888 A1 | 8/2000 |
| DE | 40 28 906 C2 | 10/1992 |
| DE | 41 40 183 A1 | 6/1993 |
| DE | 41 40 184 A1 | 6/1993 |
| DE | 43 19 438 C1 | 6/1994 |
| EP | 0 607 128 B1 | 9/1997 |
| WO | WO 93/17677 A1 | 9/1993 |
| WO | WO 94/20449 A1 | 9/1994 |
| WO | WO 98/47502 A1 | 10/1998 |
| WO | WO 00/13684 * | 3/2000 |
| WO | WO 00/13684 A2 | 3/2000 |
| WO | WO 0013684 A2 * | 3/2000 |
| WO | WO 00/50019 A2 | 8/2000 |

OTHER PUBLICATIONS

Dipiro et al. Pharmacotherapy: A Pathophysiologic Approach 4th edition. (1999) p. 1434-1436).*
Merriam-Webster's Collegiate Dictionary (Merriam-Webster Incorporated: Springfield, Massachusetts, 1993, pp. 311).*
M. Handel et al., "Inhibition of Transcription Factors by Anti-inflammatory and Anti-Rheumatic Drugs: Can Variability in Response be Overcome?", Clinical and Experimental Pharmacology and Physiology (2000) 27, 139-144.
M. Villanueva et al., "Equipotent Inhibition by R(–)-,S(+)- and Racemic Ibuprofen of Human Polymorphonuclear Cell Function in vitro", Br. J. Clin. Pharmac. (1993), 35, 235-242.
J. Caldwell et al., "The Metabolic Chiral Inversion and Dispositional Enantioselectivity of the 2-Arylpropionic Acids and Their Biological Consequences", Biochemical Pharmacology, vol. 37, No. 1, 1988, pp. 105-114.
P. Brooks et al., "Non-steroidal Anti-inflammatory Drugs Basis for Variability in Response", Birkhäuser Verlag, May 16-18, 1985, pp. 119-126.
A.M. Evans, "Enantioselective Pharmacodynamics and Pharmacokinetics of Chiral Non-steroidal Anti-inflammatory Drugs", Eur. J. Clin. Pharmacol, (1992) 42:237-256.
K. Williams, "Enantiomers in Arthritic Disorders", Pharmac. Ther., vol. 46, (1990), pp. 273-295.
A. Goodman Gilman, "The Pharmacological Basis of Therapeutics", Chapter 27, (1996), pp. 637-639.
L.W. Moreland et al., Phase III Trial of DMARD Failing Rheumatoid Arthritis Patients with TNF Receptor p75Fc Fusion Protein (TNFR:Fc, ENBREL™), J. Invest. Med., abstract 1998, 46:228A.
L.W. Moreland et al., "Treatment of Rheumatoid Arthritis with a Recombinant Human Tumor Necrosis Factor Receptor (p75)-Fc Fusion Protein", The New England Journal of Medicine, (1997), vol. 337, No. 3, pp. 141-147.

* cited by examiner

*Primary Examiner* — Jake M. Vu
(74) *Attorney, Agent, or Firm* — Paul D. Strain, Esq.; Strain & Strain PLLC

(57) ABSTRACT

The invention relates to the use of R-enantiomers of arylpropionic acids or the pharmacologically acceptable salts or derivatives thereof, in a pure or enriched form in contrast to the racemic compound, for the production of medicaments which inhibit the activation of nuclear transcription factor AP-1 and which are suitable for treating illnesses which are influenced by said factor.

27 Claims, 1 Drawing Sheet

USE OF R-ARYLPROPIONIC ACIDS FOR TREATING ILLNESSES WITH A RHEUMATIC NATURE

The subject of the present invention is the use of R-arylpropionic acids for the production of medicaments for the treatment of diseases which can be therapeutically influenced by the inhibition of the activation of the nuclear transcription factor AP-1, especially diseases of rheumatic nature.

Under the term rheuma there fall several hundred diseases in the domain of the apparatus of movement (e.g. joints, joint capsules, musculature or tendons) or of the connective tissue structures (present almost everywhere in the body) which are characterised by painful or inflammatory processes. Above all in the case of chronic courses of joint diseases due to wear (arthroses) or joint diseases due to inflammation (arthritis), the cartilage or the bones can be attacked and, in the worst cases, also the organs.

The treatment of rheumatic diseases depends, in the case of individual patients, on the severity and aggressiveness of the disease. Besides other therapeutic measures, the medicamentary rheumatherapy has a high value. Dependent on the state of the disease, medicaments are placed in 5 main groups:

1. purely anodyne, e.g. paracetamol, metamizol, tramadol
2. non-steroidal inflammation inhibitors (NSAR/NSAID): e.g. diclofenac, ibuprofen, flurbiprofen, naproxen, indomethacin, piroxicam, meloxicam, as well as more recently COX-2 inhibitors, e.g. celecoxib, rofecoxib
3. corticosteroids: e.g. cortisone, prednisone, prednisolone, dexamethasone
4. long-acting anti-rheumatics (so-called "basis medicaments"): e.g. gold salts, methotrexate, sulpha-salazine, chloroquine, cyclosporin
5. modifiers of the biological reactions ("biological therapies"): e.g., the substances leflunomide and etanercept newly allowed in some countries.

Ideal rheuma agents which, on the one hand, rapidly ameliorate the pain and inflammation symptoms and, on the other hand, help to prevent long term the destruction of the joints could hitherto not be found. Therefore, in the case of acute disease conditions, rather purely pain and inflammation inhibitors, as well as the strongly inflammation-inhibiting corticosteroids are used. For the avoidance of the long-term damages, the disease-modifying basis therapeutics are additionally used. They can check the joint destruction, introduce a regression of the disease or contribute to a certain repair of the damages already occurred.

All above-mentioned medicaments (No. 1 to 4) display, besides the desired actions, significantly undesired actions. Therefore, also for experienced therapeutists, it is often difficult to determined the optimum scheme of treatment for the individual patients with use-risk points of view. Especially the use of the long-acting antirheumatics proves to be difficult because, in part, they show only after months the desired disease-modifying action but the undesired actions can appear immediately. If long-acting medicaments, such as gold salts, are discontinued too soon, the effectiveness in the case of a further use becoming necessary decreases. Because of the disadvantages of the known medicamentary treatment schemes, with the newest molecular-biological methods it is attempted purposefully to engage modulatingly in the biochemical mechanisms of the inflammation and pain happenings. On the substances leflunomide and etanercept, just developed ready for marketing, rest great hopes to achieve desired therapeutic actions without the known undesired actions of the other groups of substances (Moreland, L. W.: Treatment of rheumatoid arthritis with a recombinant tumor necrosis factor receptor 8p75-Fc fusion protein, N. Engl. J. Med., 337 (1997), 141; Moreland, L. W., et al., Phase III trial of DMARD failing rheumatoid arthritis patients with TNF receptor p75Fc fusion protein (TNFR:Fc, ENBREL), J. Invest. Med 46: 228A (abstract) 1998). Comprehensive experiences with these substances are not yet available. The hoped for therapeutic advance must first be shown.

The invention has set itself the task of finding active materials which are able, within the disease occurrence, to prevent the joint destruction like basic therapeutics (No. 4) without causing the known main side effects.

This property profile, not to be combined in the of the previous substance classes (No. 1 to 4), could surprisingly be found in the case of substances of the arylpropionic acid group which, as is known, belong to the substance group of the non-steroidal anti-rheumatics (No. 2). Substances of this group have, in part, been known for several decades as differingly strong pain-, inflammation- and fever-inhibiting (Propionic acid derivatives: Goodman & Gilman's, The pharmacological basis of therapeutics, Chapter 27, p. 637 (1996)). These actions are essentially attributed to the direct inhibition of the isoenzymes COX-1 and COX-2. These properties bring about not only the desired but also the undesired actions of these substances.

Arylpropionic acid compounds with an asymmetric carbon atom display a centre of chirality and consequently occur as S-enantiomer and as R-enantiomer. In the case of the chemical synthesis, these active materials are usually obtained as racemates, i.e. as equal mixtures between the two enantiomers. As far as S-naproxen (Williams: Enantiomers in arthritic disorders; Pharmac. Ther., Vol. 46, pp 273-295 (1990); Evans: Enantioselective pharmacodynamics and pharmaco-kinetics of chiral non-steroidal anti-inflammatory drugs, Eur. J. Clin. Pharmacol, 42: 237-256 (1992)) and recently dexibuprofen (Symposium: Update on s(+)– ibuprofen; Going/Kitzbühel, Feb. 2-4, 1996) and dexketo profen (First launch of dexketoprofen, Scrip No. 2144: 16 (1992)), these substances have hitherto been used as racemates.

It was known that, with regard to the COX inhibition, differences exist between the enantiomeric forms of the arylpropionic acids. The COX inhibition was only ascertained in the case of the S-enantiomers whereas it was not found in the R-enantiomers in the therapeutic concentration range (Williams (v. supra); Evans (v. supra); Brooks and Day: New non-steroidal anti-inflammatory drugs, Birkhauser Verlag, Basel, p. 119-126 (1985)). Consequently, the desired therapeutic effects but also the undesired actions connected with the COX inhibition were ascribed to the S-enantiomers as they are used in pure form or to the half in the racemate. In the case of substances which in the organism are partly inverted from the R-enantiomers to the S-enantiomers, an indirect action according to the inversion quotient is assumed (Caldwell et al., The metabolic chiral inversion and dispositional enantioselectivity of the 2-arylpropionic acids and their biological consequences, Biochemical Pharmacology, Vol. 37, No. 1. pp. 105-114 (1988). This inversion is clearly marked in the case of ibuprofen in humans and all investigated animal species. Besides the indirect action by inversion to S-ibuprofen, on the basis of in vitro experiments, a direct action of R-ibuprofen via an inhibition of polymorphic nuclear leukocytes participating in the inflammation happenings is speculated (Villanueva et al., Equipotent inhibition by R(−), S(+)– and racemic ibuprofen of human polymorphonuclear cell function in vitro, Br. J. Clin. Pharmac., 35, 235-242 (1993)). A therapeutic relevance of this mechanism could hitherto not be shown.

Later, it was found that also R-enantiomers of the arylpropionic acid group, e.g. R-flurbiprofen and R-keto-profen, show their own pain-ameliorating and inflammation-inhibiting action when they are used in suitable dosing in the case of humans or animals (DE 40 28 906 C2; EPO 607 128 B1; U.S. Pat. Nos. 5,206,029 and 5,200,198; DE 43 19 438 C1; WO 93/17677). The reaction could not be explained with a direct COX inhibition. In WO 00/50019 and WO 98/47502, it is described that R-flurbiprofen in the case of concentrations higher than the pain-ameliorating acting ones in the previously used racemate inhibit the activation of the transnuclear transcription factor NF-kappa B in the case of inflammatory reactions. Because of the central position of NF-kappa B in the inflammation and immune happenings, from this discovery could be deduced new therapeutic possibilities of use of R-flurbiprofen and other inversion-stable R-arylpropionic acids or new dosaging schemes in the case of the use of these substances. In a further Patent Application (WO 00/13684) is claimed the use of R-arylpropionic acids for the inflammation inhibition in animals, whereby the manner of action is ascribed to an inhibition of the biosynthesis of COX-2 on the COX-2 mRNA plane. An inhibition of the COX-2 synthesis on this plane could lead to an inhibition not only of the inducible COX-2 in the case of inflammatory reactions but also of the constitutively present (physiologically necessary in the non-inflammatory state) COX-2. Thus, substances according to this working mechanism, also without the direct COX-2 inhibition, would show the same side effect potential as the new direct COX-2 inhibitors. In this invention, it is not given to what extent the action of R-arylpropionic acids depends upon the inversion to the highly-effective S-arylpropionic acids which is very marked in most animal species and which, in the case of the highly used dosages of the R-arylpropionic acids, could easily lead to effective concentrations of S-arylpropionic acids.

All previously known knowledge of the manner of action of the R-arylpropionic acids predestine this group of active materials for use as pain-ameliorating and inflammation-inhibiting medicaments with short period of action. Thus, the initially described classes of medicaments are to be allocated between the pure pain agents (No. 1) and the non-steroidal inflammation-inhibiting active agents (No. 2). Therapeutic advantages going beyond this were hitherto not to be expected since, with Patent Application WO 00/50019, the therapeutic possibilities could best be explained with the new scientific knowledge.

Surprisingly, however, it was now found that substances of the R-arylpropionic acid group, besides the described short-term actions, also display actions which make them suitable for the use as disease-modifying medicaments. This means that, on the basis of the newly discovered actions, they are able modulatingly to engage in the mechanism of the long-term bone and cartilage destruction. This action is otherwise only given for the slow and long-acting basis therapeutics (No. 4) which, however, display a substantially wider side effect spectrum.

The disease-modulating action is caused via the inhibition of the activation of activator protein 1 (AP-1) ascertained according to the invention. The inhibition of the AP-1 activation inhibits the over-expression of proteins, such as e.g. metalloproteinases, collagenase and stromelysine, which are brought into conjunction with the metabolic processes in the joint. Direct or indirect erosive processes, which play a part in the bone breakdown can therewith be reduced (Handel, M. L. et al.: Inhibition of transcription factors by anti-inflammatory and anti-rheumatic drugs: Can variability in response be overcome?, Clinical and Experimental Pharmacology and Physiology (2000) 27, 139-144). Of some substances, e.g. of dexamethasone, it is known that they inhibit the activation of NF-kappa B which stands in agreement with their strong inflammation-modifying properties. The basis therapeutics gold thiolate and D-penicillamine inhibit the AP-1 activation which, in turn, stands in agreement with the disease-modifying action. Due to the inflammation inhibition of the R-arylpropionic acids known from (WO 00/50019) via the inhibition of the NF-kappa B activation in combination with the newly discovered disease-modifying action via the inhibition of the activation of AP-1, this substance group combines many desired properties of other substance groups without showing their unfavourable side effect profile. Via the inhibition of the activation of AP-1, there can therewith also be inhibited the connected over-expression of cytokines, such as TNF-alpha. In this regard, it can be expected that R-arylpropionic acids, besides the described actions, also display similar actions like the new direct inhibitors of TNF-alpha (see No. 5).

Besides the newly found action, which requires a long-term use, such agents naturally also show the known short-term action of the pain and inflammation inhibitions. Thus, for the first time, R-arylpropionic acids exercise a double function by rapid engagement in the pain and inflammation happenings, as well as by inhibition of the erosive-degenerative progressing joint processes. Expressed in other words, with one active material there is treated not only symptom-modifyingly but also disease (course) modifyingly. At the same time, the substantially undesired actions of the medicament groups otherwise to be used separately are avoided. Since the short term inflammation-inhibiting action of sufficiently highly dosed R-arylpropionic acids in the experimental model is equally or better marked as in the case of the strongly effective corticosteroid dexamethasone, R-aryl-propionic acids are also ideal partners for a combination therapy together with basis therapeutics, on the widely positioned effectiveness of which can, at the moment, not be relinquished. The combination therapy between non-steroidal inflammation inhibitors or corticosteroids and basis therapeutics in one of the standard therapy processes in rheumatology.

The pharmaceutical formulations of the present invention include R-arylpropionic avid as active material or a pharmaceutically compatible derivative thereof and a pharmaceutically compatible carrier material and, if desired, other therapeutic additives.

The manners of expression "pharmaceutically compatible derivatives" or "a pharmaceutically compatible derivative thereof refer to derivatives prepared from pharmaceutically compatible non-toxic acids or bases, including inorganic acids and bases and organic acids and bases. Since the component of the present invention is acidic, derivatives with pharmaceutically compatible non-toxic bases, including inorganic and organic bases, can be prepared. Suitable pharmaceutically compatible basic additive derivatives for the components of the present invention include metal salts prepared from aluminium, calcium, lithium, magnesium, potassium, sodium and zinc or organic salts prepared from lysine, N,N'-dibenzyl-ethylenediamine, choline, diethanolamine, ethylene-diamine, meglumine (N-methylglucamine), tromethamine and alkylamines with 1-6 C-atoms.

The formulations of the present invention include formulations such as suspensions, solutions, elixirs and aerosols. Carrier materials, such as starch, sugar, microcrystalline cellulose, diluents, granulation adjuvants, lubricants, binding agents, solvents and the like can be used in the case of solid oral forms of administration. Solid oral forms of administration (such as powders, capsules and tablets) are preferred to the liquid oral forms of administration. The preferred solid forms of administration are tablets. If desired, the tablets can be coated with standardised water or water-free coating agents.

Pharmaceutical formulations of the present invention which are suitable for the oral forms of administration can, as separate units, such as capsules, dragees or tablets, or aerosols each contain a predetermined amount of the active material in the form of powder or granulate, or as solution or suspension in an aqueous liquid, or a non-aqueous liquid, an oil-in-water or liquid water-in-oil emulsion. Such formulation can be produced according to any pharmaceutical methods but all methods comprise a mixing of the active material with a carrier substance which consists of one or more of the necessary components. In general, the formulations are produced by uniform and thorough mixing of the active material with liquid carrier substances or finely comminuted solid carrier substances or both and then, if necessary, forming of the product into the desired form of administration.

For example, a tablet can be produced by pressing or forming, if desired with one or more additional components. Pressed tablets can be produced in appropriate devices when the active material is present in flowable form, such as powder or granulate, if desired mixed with a binding agent, lubricant, inert diluent, dispersion or surface-active agent. Formed tablets can also be produced by forming of a mixture of pulverised components, moistened with an inert liquid diluent, in a suitable device and subsequent drying. Preferably, each tablet contains between 30 mg and 1200 mg of the active material and each dragee or capsule contains between about 50 mg and about 600 mg of the active material. Especially preferred, each tablet, dragee or capsule contains one of four dosages, namely, 50 mg, 100 mg, 200 mg or 500 mg of the active material.

EXAMPLE

The inhibition of the activation of AP-1 was shown with a pharmacological model. For this purpose, a cell culture of the murine macrophage cell line RAW 264-7 was taken and stimulated with 10 mg/ml LPS for 1 hour in the absence or in the presence of flurbiprofen. R-flurbiprofen (0.1, 1, 10, 100 and 1000 µM) and S-flurbiprofen (0.1, 1, 10, 100 and 1000 µM) were dissolved in phosphate buffer, added to the cell cultures 30 minutes before the LPS treatment. After conclusion of the treatment, the cells were harvested and worked up in a cytosol fraction and a cell nucleus extract. The cell nucleus extract (5-10 g) was incubated for 30 minutes with the AP-1-specific oligonucleotide 5'-CGCTT GATGACTCAGCCGGAA-3' which is terminally labelled with $^{32}P$ ATP. From the incubation medium was separated the nucleus protein DNA complexes from the non-bound DNA by electro-phoresis (electrophoretic mobile shift assay EMSA). After drying of the gels, these were visualised by means of autoradiography. Typical results are shown in FIG. 1. They show that the specific AP-1 binding activity in LPS-stimulated cells has clearly increased in comparison with unstimulated control cells. R-flurbiprofen (10-1000 µM) inhibits the AP-1 DNA binding dosage-dependent. In the case of 1000 µM, it was completely suppressed. With S-flurbiprofen, a reduction was found only in the case of the highest concentration of 1000 µM.

In some embodiments, as the R-arylpropionic acid compound, there are used R-flurbiprofen or its derivatives. In some embodiments, the compounds R-ketoprofen, R-naproxen, R-tiaprofenic acid or R-fenoprofen, scarcely inverted in the case of humans, or pharmacologically compatible salts or derivatives of these compounds are used.

Figure 1:
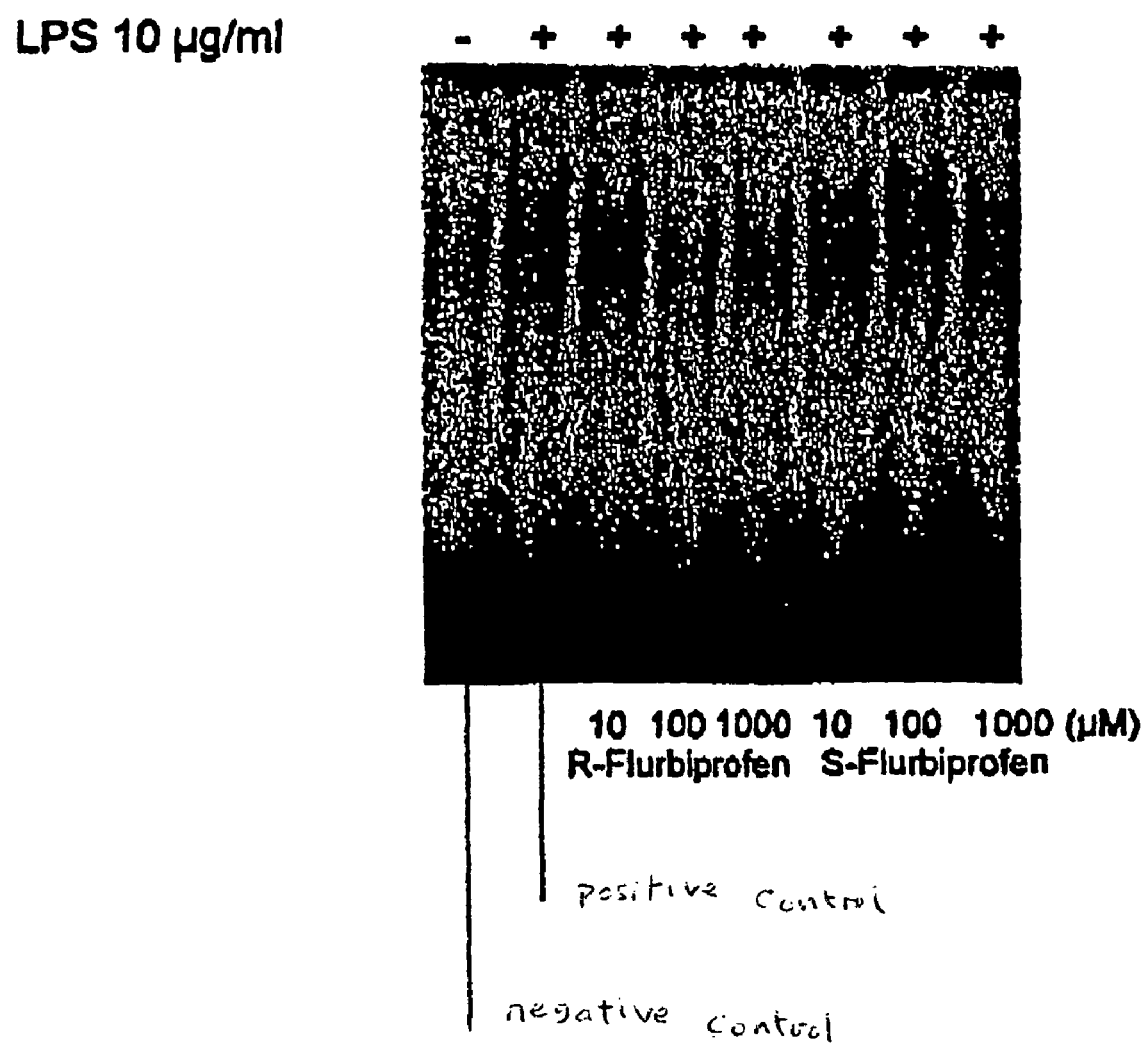
FIG. 1 shows the effects of R-flurbiprofen and S-flurbiprofen on the DNA binding activity of AP-1 in LPS-stimulated murine macrophages, determined by EMSA.

What is claimed is:

1. A method for treating the erosive-degenerative progressing joint processes of at least one joint and/or cartilage comprising administering to a patient in need thereof as a slow and long-acting basis therapeutic for a period of time effective to at least prevent the long term destruction of the at least one joint and/or cartilage an effective dose comprising one or more compounds selected from R-flurbiprofen, R-ketoprofen, R-naproxen, R-tiaprofenic acid, and R-fenoprofen, their pharmacologically compatible salts, in a pure form or, in comparison with the racemate, in an enriched form.

2. A method of claim 1, wherein the one or more compounds are selected from R-flurbiprofen, or its pharmacologically compatible salts.

3. A method of claim 1, wherein the one or more compounds are selected from R-ketoprofen, R-naproxen, R-tiaprofenic acid, and R-fenoprofen, pharmacologically compatible salts.

4. A method of claim 3, wherein the one or more compounds are scarcely inverted to S-enantiomers of an arylpropionic acid and the patient is a human.

5. A method of claim 1, wherein the effective dose includes at least one basis therapeutic selected from gold salts, methotrexate, sulpha-salazine, chloroquine, and cyclosporin as an additional active ingredient.

6. A method of claim 1, wherein the effective dose comprises an amount of active materials ranging from 30 mg to 1200 mg per dose.

7. A method of claim 1, wherein the effective dose comprises an amount of active materials ranging from 60 mg to 3600 mg daily.

8. A method of claim 1, wherein the one or more compounds are present in a free form, as a salt with inorganic or organic salt forming substances or as a complex or as an acid ester or an acid amide.

9. A method of claim 1, wherein the one or more compounds are administered in a form of a pharmaceutical formulation obtained by addition of one or more pharmaceutical adjuvants.

10. A method of claim 9, wherein the pharmaceutical formulation is selected from tablets, capsules, dragees, drink granulates, drink tablets, drops, chewable formulations, injection solutions, ointments, gels, topical spray solutions, plasters, solid inhalation formulations, liquid inhalation formulations, and suppositories.

11. A method for treating the erosive-degenerative progressing joint processes of at least one joint and/or cartilage consisting essentially of administering to a patient in need thereof as a slow and long-acting basis therapeutic for a period of time effective to at least prevent the long term destruction of the at least one joint and/or cartilage an effective dose comprising one or more compounds selected from R-flurbiprofen, R-ketoprofen, R-naproxen, R-tiaprofenic acid, and R-fenoprofen, their pharmacologically compatible salts, in a pure form or, in comparison with the racemate, in an enriched form.

12. A method of claim 11, wherein the one or more compounds are selected from R-flurbiprofen, its pharmacologically compatible salts.

13. A method of claim 11, wherein the one or more compounds are selected from R-ketoprofen, R-naproxen, R-tiaprofenic acid, and R-fenoprofen, pharmacologically compatible salts.

14. A method of claim 13, wherein the one or more compounds are scarcely inverted to S-enantiomers of an arylpropionic acid and the patient is a human.

15. A method of claim 11, wherein the effective dose includes at least one basis therapeutics selected from gold salts, methotrexate, sulpha-salazine, chloroquine, and cyclosporin as an additional active ingredient.

16. A method of claim 11, wherein the effective dose comprises an amount of active materials ranging from 30 mg to 1200 mg per dose.

17. A method of claim 11, wherein the effective dose comprises an amount of active materials ranging from 60 mg to 3600 mg daily.

18. A method of claim 11, wherein the one or more compounds are present in a free form, as a salt with inorganic or organic salt forming substances or as a complex or as an acid ester or an acid amide.

19. A method of claim 11, wherein the one or more compounds are administered in a form of a pharmaceutical formulation obtained by addition of one or more pharmaceutical adjuvants.

20. A method of claim 19, wherein the pharmaceutical formulation is selected from tablets, capsules, dragees, drink granulates, drink tablets, drops, chewable formulations, injection solutions, ointments, gels, topical spray solutions, plasters, solid inhalation formulations, liquid inhalation formulations, and suppositories.

21. A method for treating the erosive-degenerative progressing joint processes of at least one joint and/or cartilage consisting of administering to a patient in need thereof as a slow and long-acting basis therapeutic for a period of time effective to at least prevent the long term destruction of the at least one joint and/or cartilage an effective dose consisting of one or more compounds selected from R-flurbiprofen, R-ketoprofen, R-naproxen, R-tiaprofenic acid, and R-fenoprofen, their pharmacologically compatible salts, in a pure form or, in comparison with the racemate, in an enriched form.

22. A method for treating the erosive-degenerative progressing joint processes of at least one joint and/or cartilage comprising identifying a patient in need of treating the erosive-degenerative progressing joint processes of at least one joint and/or cartilage and administering to a patient in need thereof as a slow and long-acting basis therapeutic for a period of time effective to at least prevent the long term destruction of the at least one joint and/or cartilage an effective dose comprising one or more compounds selected from R-flurbiprofen, R-ketoprofen, R-naproxen, R-tiaprofenic acid, and R-fenoprofen, their pharmacologically compatible salts, in a pure form or, in comparison with the racemate, in an enriched form.

23. A method for treating the erosive-degenerative progressing joint processes of at least one joint and/or cartilage comprising identifying a patient in need of treating the erosive-degenerative progressing joint processes of at least one joint and/or cartilage and administering to a patient in need thereof as a slow and long-acting basis therapeutic for a period of time effective to at least prevent the long term destruction of the at least one joint and/or cartilage an effective dose consisting of one or more compounds selected from R-flurbiprofen, R-ketoprofen, R-naproxen, R-tiaprofenic acid, and R-fenoprofen, their pharmacologically compatible salts, in a pure form or, in comparison with the racemate, in an enriched form.

24. A method for treating the erosive-degenerative progressing joint processes of at least one joint and/or cartilage comprising administering to a human in need thereof as a slow and long-acting basis therapeutic for a period of time effective to at least prevent the long term destruction of the at least one joint and/or cartilage an effective dose comprising one or more compounds selected from R-flurbiprofen, its pharmacologically compatible salts, in a pure form or, in comparison with the racemate, in an enriched form.

25. A method for treating long term bone and/or cartilage destruction, comprising administering to a patient in need thereof as a slow and long-acting basis therapeutic an effective dose in order to at least prevent the long term bone and/or cartilage destruction, wherein the effective dose comprises one or more compounds selected from R-flurbiprofen, R-ketoprofen, R-naproxen, R-tiaprofenic acid, and R-fenoprofen, pharmacologically compatible salts, in a pure form or, in comparison with the racemate, in an enriched form.

26. A method for preventing long term destruction of bone and/or cartilage in erosive-degenerative progressing joint processes of at least one joint and/or cartilage, comprising administering to a patient in need thereof as a slow and long-acting basis therapeutic an effective dose in order to at least prevent the long term destruction of bone and/or cartilage, wherein the effective dose comprises one or more compounds selected from R-flurbiprofen, R-ketoprofen, R-naproxen, R-tiaprofenic acid, and R-fenoprofen, pharmacologically compatible salts, in a pure form or, in comparison with the racemate, in an enriched form.

27. A method for treating the erosive-degenerative progressing joint processes of at least one joint and/or cartilage comprising administering to a patient in need thereof as a slow and long-acting basis therapeutic to at least prevent the long term destruction of the at least one joint and/or cartilage an effective dose in order to at least prevent the long term destruction of bone and/or cartilage, wherein the effective dose comprises one or more compounds selected from R-flurbiprofen, R-ketoprofen, R-naproxen, R-tiaprofenic acid, and R-fenoprofen, pharmacologically compatible salts, in a pure form or, in comparison with the racemate, in an enriched form.

* * * * *